United States Patent

Constable et al.

[11] Patent Number: 6,148,742
[45] Date of Patent: Nov. 21, 2000

[54] APPARATUS FOR DISPOSING OF HYPODERMIC NEEDLES

[75] Inventors: Nicholas John Constable, Surrey; David Wong, London, both of United Kingdom

[73] Assignee: Needle Incinerator Company Limited, London, United Kingdom

[21] Appl. No.: 08/945,496

[22] PCT Filed: Apr. 24, 1996

[86] PCT No.: PCT/GB96/00976

§ 371 Date: Dec. 22, 1997

§ 102(e) Date: Dec. 22, 1997

[87] PCT Pub. No.: WO96/33758

PCT Pub. Date: Oct. 31, 1996

[30] Foreign Application Priority Data

Apr. 26, 1995 [GB] United Kingdom ............ 9508516
Aug. 1, 1995 [GB] United Kingdom ............ 9517056

[51] Int. Cl.[7] .................. F23G 5/40; F23G 5/50; F23G 7/00; B65D 83/02
[52] U.S. Cl. .......... 110/250; 110/185; 110/241; 110/242; 219/68; 206/365; 220/908
[58] Field of Search .............. 110/185, 233, 110/235, 241, 242, 250, 249, 346; 219/50, 68; 206/365, 366; 220/908

[56] References Cited

U.S. PATENT DOCUMENTS

| | | |
|---|---|---|
| 4,351,434 | 9/1982 | Elisha ................................ 206/366 |
| 4,531,437 | 7/1985 | Szablak et al. . |
| 4,877,934 | 10/1989 | Spinello . |
| 5,003,892 | 4/1991 | Bricken ................................ 110/346 |
| 5,076,178 | 12/1991 | Kohl et al. . |
| 5,138,124 | 8/1992 | Kirk et al. ............................ 219/68 |
| 5,171,387 | 12/1992 | Wuchinich . |
| 5,259,501 | 11/1993 | Withers et al. . |
| 5,268,549 | 12/1993 | Butler ................................. 219/68 |
| 5,282,428 | 2/1994 | Greville et al. ..................... 110/250 |
| 5,384,029 | 1/1995 | Campbell . |
| 5,637,238 | 6/1997 | Truesdale et al. ................... 219/68 |

FOREIGN PATENT DOCUMENTS

| | | |
|---|---|---|
| 0 283 226 | 9/1988 | European Pat. Off. . |
| 92/12818 | 8/1992 | WIPO . |
| 93/25250 | 12/1993 | WIPO . |
| 94/01153 | 1/1994 | WIPO ................................. 110/250 |
| 94/07543 | 4/1994 | WIPO . |
| 94/22512 | 10/1994 | WIPO . |

*Primary Examiner*—Ira S. Lazarus
*Assistant Examiner*—Ljiljana V. Ciric
*Attorney, Agent, or Firm*—Smith-Hill and Bedell

[57] ABSTRACT

A needle incineration apparatus for disposing of hypodermic needles comprises an insertion aperture (26) through which a needle to be destroyed may be introduced into the apparatus, two electrodes separated by a gap that is aligned with the insertion aperture (26), and a power supply for applying a voltage across the electrodes to destroy needles introduced through the insertion aperture (26) into the gap to contact the two electrodes. In accordance with the invention, the apparatus is formed of a main housing (10) and a disposable cartridge (20) separable from the main housing (10), the power supply being disposed within the main housing (10), the insertion aperture (26) being formed in a wall of the cartridge (20) and the electrodes being disposed in the cartridge (20) within a permanently closed compartment for storing debris resulting from the destruction of the needles.

23 Claims, 2 Drawing Sheets

APPARATUS FOR DISPOSING OF HYPODERMIC NEEDLES

The present invention relates to apparatus for destroying the needles of hypodermic syringes to permit their safe disposal.

BACKGROUND OF THE INVENTION

Disposal of hypodermic syringes having needles attached to them, presents a serious risk of infection to the handlers, especially if they should accidentally prick themselves on one of the needles.

Various forms of apparatus have therefore previously been is proposed that pass a current through the needles to destroy them, this being commonly termed needle incineration. The current not only melts the needles to prevent them from pricking a handler of the waste hypodermic syringes, but also burns off any toxic residue on the needles.

Such apparatus usually has two spaced electrodes that apply a low voltage across a short length of the needle near its tip and the high current that flows melts this section of the needle. The needle is then progressively fed through the gap between the electrodes to melt the whole of the needle down to the collar that is fitted to the syringe.

The electrodes that are used to pass a current through the needles tend to corrode with time and to facilitate their replacement it has been proposed in GB-A-2,278,986 to mount the electrodes on a cartridge-like electrode plate unit having syringe insertion holes. This facilitates the task of clearing debris from the vicinity of the electrodes, which will themselves be contaminated with pathogens, the debris from the needles is stored in an open box which still presents a hazard to the person emptying the incineration apparatus as it fills up with use, because the debris and the box are contaminated both from any drips from the syringe and from the aerosol action.

U.S. Pat. No. 5,076,178 discloses an apparatus that has an incinerator housing that is separate from a power supply housing and from a drawer for storing the hypodermic syringes. Though termed an incinerator housing, the incineration electrodes and a sealing crimp do not in fact form part of the incinerator housing but remain attached to the power supply housing when the incinerator housing is withdrawn for emptying. The apparatus does not therefore avoid the possibility of contamination by coming into contact with the needle debris.

A further apparatus, disclosed in U.S. Pat. No. 4,877,934, has a drawer with an elongate slot in its top surface alongside which one of the electrodes is provided to contact the needle to be incinerated near to the hub. A second electrode is disposed on a ramped surface on the bottom of the drawer opposite the elongate slot. In use, the needle is moved along the elongate slot and first heated over its entire length. As the needle is incinerated it is moved up the ramp to destroy to reduce its length progressively.

The drawer in this case is not permanently closed because debris can escape from the drawer. Furthermore, one of the electrodes, which can itself be contaminated, is exposed on the upper surface of the drawer. For this reason, a cover needs to be fitted to seal the top of the drawer for safety before it is discarded.

OBJECT OF THE INVENTION

The present therefore seeks to minimise the risk of infection to a handler both from the sharp needles and from the debris created by passing a current through the needles.

SUMMARY OF THE INVENTION

According to a first aspect of the present invention, there is provided a needle incineration apparatus for disposing of hypodermic needles comprising an insertion aperture through which a needle to be destroyed may be introduced into the apparatus, two spaced electrodes defining therebetween a gap aligned with the insertion aperture and a power supply for applying a voltage across the electrodes to destroy needles introduced through the insertion aperture into the gap to contact the two electrodes, wherein the apparatus is formed of a main housing and a disposable cartridge separable from the main housing, the power supply being disposed within the main housing and the insertion aperture being formed in a wall of the cartridge, characterised in that the electrodes are mounted in the cartridge within a sealed debris compartment for retaining debris resulting from the destruction of the needles.

Because the debris compartment is sealed, debris cannot at any time leave nor be emptied from the compartment, not even through the insertion aperture. As a result, it is not necessary, nor indeed is it possible, at any time to come into contact with the debris. Once the cartridge is full of debris, it cannot be emptied and it must instead be replaced complete with the contained electrodes.

Furthermore, because the storage compartment for the debris is permanently closed, no special precautions need to be taken when handling a full cartridge, The invention is thus to be contrasted with the apparatus described in the above mentioned U.S. Pat. No. 4,877,934 where it is necessary to fit a cover to the cartridge to ensure that the debris does not escape unintentionally and cause contamination.

In known needle incineration apparatus, special steps need to be taken to prevent a build-up of a deposit on the electrodes as such a deposit can eventually prevent the apparatus from functioning correctly. Hence, GB-A-2,273,231, for example, proposes forming one of the electrodes as a rotatable drum. In the present invention, the need to take special steps to prevent the build-up of a deposit will depend, for example, on the size of the cartridge. If the cartridge is small, as in an apparatus intended for home use, then it is not necessary to take any steps to prevent the build up of such a deposit if it is not likely to impair the operation of the apparatus before the compartment fills up with needle debris.

In an apparatus having a larger cartridge, however, it is preferred in a second aspect of the invention to provide means for vibrating at least one of the electrodes in the cartridge to inhibit the build-up of a deposit on the electrodes.

An electrode in the cartridge could be vibrated by means of a vibrator mounted in the main housing if a suitable mechanism is provided to transmit the vibrations through the interface between the main housing and the cartridge. However, in order to avoid unnecessary complexity, it is preferred to mount within the cartridge means for vibrating one of the electrodes.

Though an electromagnetic device could be used as a vibrator, it is preferred to use a piezoelectric crystal. Such a vibrator has no movable parts that can perish during the useful life of the cartridge and is sufficiently inexpensive not to add unduly to the cost of the disposable cartridge. It can also be more compact and lighter than an electromagnetic vibrator, A still further advantage of the use of a piezoelectric crystal as a vibrator is that it can be made to oscillate at ultrasonic frequencies so that noise generated by the apparatus during operation will not be perceptible, at least to humans.

As a needle is incinerated, fumes are emitted and a spray can be produced by the aerosol action of heating a needle that still contains a fluid. It is preferred therefore that the compartment in the cartridge should not only be closed but sealed, at least during the time that a current is being passed through the needle. To this end, the insertion aperture, which is required to accommodate hypodermic syringes of different diameter, may be fitted with a sealing bellows of elastomeric material at the centre of which is mounted a more rigid conical guide member having a central hole for the passage of the needle into the compartment.

It is further preferred to provide a self-closing membrane across the mouth of the bellows. This could for example comprise a sheet of elastomeric material that has one or more slits to define flaps that will separate automatically during the insertion of a syringe and will return to a closed mating position when the syringe is withdrawn from the insertion aperture. In this way, egress of fumes from the cartridge can be inhibited even after the syringe has been withdrawn from the insertion aperture.

If the gap between the electrodes is of constant size, then there will always remain a short length at the end of a needle that cannot be melted and this short stub can still present a minor hazard to an operator. The hazard is only minor because the tip will not be sharp, it will in most cases have been sealed by melting and it will also have been heated sufficiently to sterilise it and destroy pathogens.

Nevertheless, it is preferred to mount one of the electrodes to be movable towards the other to close the gap between the electrodes as the end of a needle is reached. The electrodes may be pushed towards one another by the collar of the needle that is fitted to the hypodermic syringe. Though the movable electrode may be supported in any suitable manner, for example for sliding movement, it is preferred that it should be pivotably mounted within the cartridge.

One can form the cartridge with a transparent wall section so that visual inspection would suffice to determine when the cartridge is full and in need of replacement. Alternatively, however, one may provide means for sensing the level of the debris within the debris compartment of the cartridge. Such sensing means preferably relies on the electrical conductivity of the debris and comprises two spaced electrodes of which at least one is positioned in the cartridge near the maximum debris level. A more costly alternative that does not rely on the conductivity of the debris would be to resort to optical level sensing, relying on the debris interrupting the light path between a light source and a photosensitive device.

The invention also provides in accordance with a further aspect a cartridge for a needle incineration apparatus having an electrical power supply disposed within a main housing, the cartridge comprising a container capable of being releasably fitted to the main housing and having an internal permanently closed debris compartment, two electrodes disposed within the debris compartment, an insertion aperture in the wall of the container for enabling a needle to be destroyed to be inserted into the debris compartment to make contact with the electrodes and at least one electrical connector on the exterior of the container for connecting the electrodes in the cartridge to the electrical power supply in the main housing when the cartridge is fitted to the housing.

BRIEF DESCRIPTION OF THE DRAWINGS

The invention will now be described further, by way of example, with reference to the accompanying drawings, in which.

DESCRIPTION OF THE PREFERRED EMBODIMENT

Figure 1:
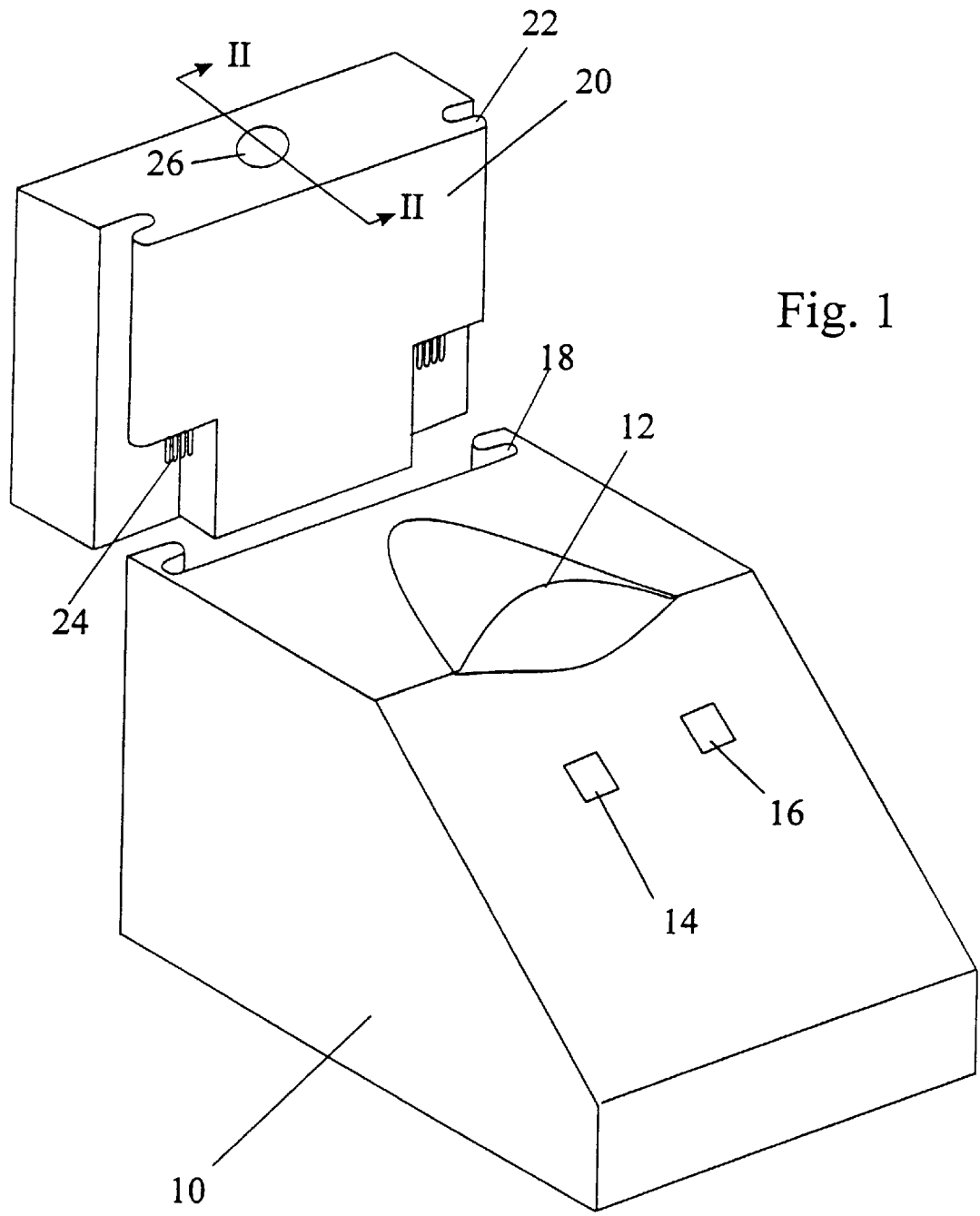
FIG. 1 shows an external perspective view of one embodiment of a needle incineration apparatus in accordance with the present invention.

The needle incineration apparatus of FIG. 1 comprises a main housing 10 and a cartridge 20. The main housing 10 is formed with an integral carrying handle 12 and has two indicator lights 14 and 16. The light 14 indicates that the apparatus is live, that is to say connected to a mains supply, and the light 16 is used to indicate that the cartridge 20 is full and in need of replacement.

The main housing contains a transformer, a control circuit and a cut-out device, that is to say a fuse or a circuit breaker, the operation of which will be described below. It is not believed necessary to describe the control circuit and the design of the contents of the main housing in detail as they may be of conventional construction and their design will be clear to the person skilled in the art.

The housing 10 and the cartridge 20 have interlocking formations to enable the cartridge 20 to be fitted securely to the main housing 10. More particularly, the housing 10 has at one end two grooves 18 and the disposable cartridge 20 has two tongues 22. Once the tongues 22 have been inserted into the grooves 18, the cartridge is guided for sliding movement in a vertical direction and, at the bottom end of its travel, pins 24 of two plug connectors projecting downwards from the cartridge 20 engage in upwardly facing sockets (not shown) in the main housing to establish various electrical connections between circuit elements mounted in the cartridge 20 and the circuit mounted within the housing 10. The cartridge 20 also has an insertion aperture 26 through which needles to be destroyed can be introduced into the apparatus while they are still attached to the body of a hypodermic syringe.

The cartridge 20 is permanently closed and the only access to its interior debris compartment is through the insertion aperture 26. In operation, when needles are inserted into the aperture 26, they are incinerated in the manner described in greater detail below and all the debris that results from their destruction remains within the debris compartment of the cartridge 20. When the hypodermic syringe is withdrawn from the aperture 26, all that remains on it of the needle is the plastics attachment collar and a very small stub of the metal of the needle. This stub is not sharp and its central aperture is in most cases closed, to seal off the contents of the hypodermic syringe. Furthermore, the stub will have been heated to a temperature sufficiently high to sterilise it. As the needle has been made blunt and sterilised, one may therefore dispose of the hypodermic syringe safely without any risk of it pricking or infecting the handler of the waste material.

No contact is ever made with the needle debris and it remains within the debris compartment of the cartridge.

When the cartridge is full, the light 16 on the housing 10 indicates that the cartridge 20 is in need of replacement and all that is required of the user is to slide out the full cartridge 20 and replace it with a new empty one. The user can then dispose of the full cartridge 20 safely using the same disposal facilities as used for the hypodermic syringes that have been rendered harmless.

Figure 2:
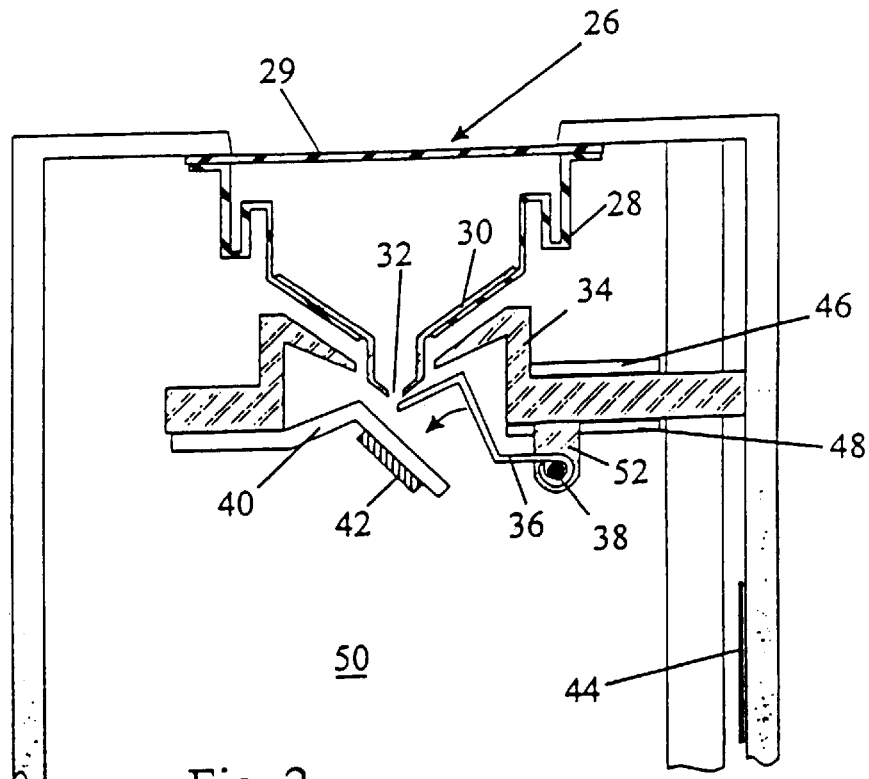
FIG. 2 shows a partial section along the line II—II in FIG. 1.
Figure 3:
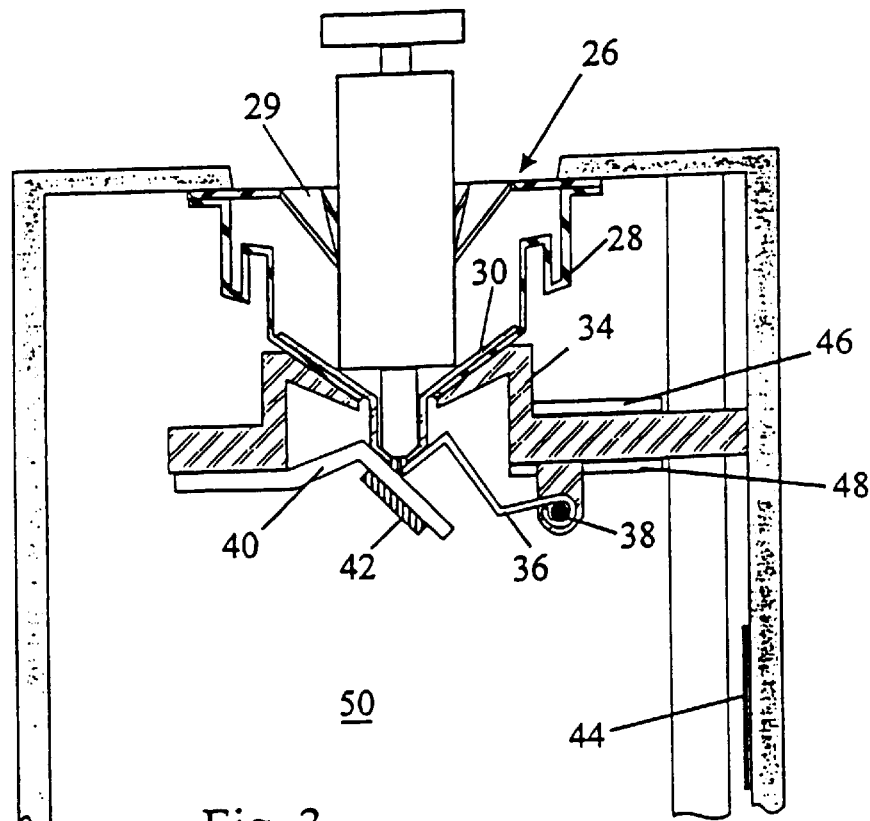
FIG. 3 is a view similar to that of FIG. 2 with a hypodermic syringe inserted into the cartridge, the view showing the position of the electrodes at the end of incineration of the needle.

Referring now to FIGS. 2 and 3, these show a partial section through the cartridge 20 in the vicinity of the insertion aperture 26. A rubber bellows 28 having a self-closing membrane 29 extending across its mouth is secured by an adhesive to the inner surface of the cartridge 20 around the aperture 26. The self-closing membrane 29 comprise a sheet of elastomeric material that has one or more slits to define flaps. The flaps separate automatically during the insertion of a syringe and return to a closed mating position when the syringe is withdrawn from the insertion aperture.

The flexible bellows 28 carries at its lower end a rigid conical plastics guide member 30 that has a small central hole 32 for passage of the needle to be incinerated. The guide member 30 can be attached to the bellows 28 by means of an adhesive but it is simpler for it to be elastically gripped by the bellows 28, the latter being stretched as it is fitted over the guide member 30. The large diameter of the guide member 30 is sufficient to accommodate the largest of hypodermic syringes and, regardless of the diameter of the syringe, the hard conical surface of the guide member guides the needle through the central hole 32.

A first electrode 36 is positioned coaxially under the hole 32 and a second electrode 40 extends below the first electrode 36 and the hole 32, so that the gap between two the electrodes 36 and 40 is aligned with the hole 32. These electrodes 36 and 40 are mounted on a separately formed support frame 34 that is held in position in the cartridge 20 by being slid into a groove defined by ribs 46, 48 projecting inwards from the side walls of the cartridge 20. The cartridge is assembled from two initially separate plastics shells and the support frame 34 is slid into the groove before the shells are permanently secured to each other, for example by an adhesive or welding,. to seal the inner compartment 50 and retain the support frame 34 in position.

It will be clear to the person skilled in the art that the manner in which the body of the cartridge is constructed may be varied without departing from the scope of the invention as set out in the appended claims. One can for example envisage the cartridge being moulded in one piece and the electrodes being incorporated within it by insert moulding or by being inserted into it through the needle insertion aperture before the latter is sealed.

In the illustrated embodiment of the invention, the support frame 34 has two depending ears 52 between which there extends a pivot pin 38 for one of the electrodes 36. A torsion spring (not shown) surrounding the pivot pin 38 acts to bias the electrode 36 clockwise as viewed, the electrode 36 being pivoted anti-clockwise, as indicated by the arrow in FIG. 2, by contact with the guide member 30 when an inserted hypodermic syringe reaches the position shown in FIG. 3.

A second electrode 40 is firmly attached to the support frame 34, for example by rivets (not shown), and carries a piezoelectric crystal 42. The crystal 42 is secured by means of an adhesive to the side of the electrode 40 facing away from the hole 32 in the guide member 30.

An adhesive strip 44 with an electrically conductive surface is stuck to the inner wall of the cartridge 20 level with the height of the debris when the cartridge is full and a similar strip (not shown) is attached to the base of the compartment. These strips 44 together form a level sensor that relies on the conductivity of the debris to determine when the cartridge is full. It is alternatively possible to use any other suitable form of level sensor. For example, an optical level sensor comprising a light source and a light sensitive device may be used, relying on the light path between the light source and light sensitive device being obstructed by the debris when the debris compartment 50 is full.

Connection wires are provided in the cartridge to connect the various circuit elements to the pins of the connectors 24 but these wires have not been shown in the drawings in the interest of clarity. Instead of using wires, conductors may be printed on the inner wall of the cartridge. These connections comprise two conductors leading from each of the electrodes 36 and 40 to a respective pair of contact pins on the connectors 24; two contact pins being used for each electrode in order to be able to support the large current required to incinerate the needles. Two conductors lead from two pins to the piezoelectric crystal 42 and two further conductors lead from the conductive strips 44 of the debris level sensor to two further pins on the connectors. When using printed conductors in place of wires, it is of course possible to dispense with the self-adhesive strip 44 and to use the conductors themselves as sensor contacts.

When a needle is to be incinerated, it is inserted while still mounted on the syringe into the cartridge 20 through the insertion aperture 26. The flaps of the membrane 29 are deflected by the body of the syringe to permit the syringe to be pushed down to the position shown in FIG. 3. During this time, a mains transformer within the main housing supplies a low voltage across the electrodes 36 and 40. This voltage may be manually switched on by the operator or it may be switched on automatically by the control circuit sensing a drop in the resistance between the two electrodes when a needle is inserted to bridge the gap between them. At the same time, an oscillator within the main housing applies an alternating excitation voltage, preferably at an ultrasonic frequency, to the piezoelectric crystal 42. Though the voltage applied across the electrodes 36 and 40 need only be low, typically 3 V, to avoid any risk of electrocution to the user, a high current will flow through the tip of the needle short circuiting the two electrodes and this will cause the metal of the needle to melt. With moderate downward pressure applied to the syringe, the needle is destroyed progressively until such time as the collar on the needle contacts the guide member 30 and pushes it down, as shown in FIG. 3. Movement of the guide member 30 is restricted by its coming into contact with a conical cup defined by the support frame 34 and at this point the guide member pushes the pivotable electrode 36 anti, clockwise as viewed, against the action of its bias spring, closing the gap between the electrodes and therefore minimising the length of the stub of the needle left on its collar.

When the needle has been fully destroyed, the user will not be able to push the syringe down any further into the aperture 26 because of the obstruction presented by the support frame 34. On meeting this increased resistance, the user should withdraw the syringe from the aperture. Should he however fail to do so for any reason, or if the electrodes should remain in contact with one another after the syringe has been withdrawn, there is a risk of overloading the power supply. To avoid permanent damage to the circuitry in the main housing 10, the latter contains a cut-out, which can be a fuse, a thermal circuit breaker or a timer that automatically cuts out after a given time. If desired, a further indicator light can be provided on the main housing to indicate that the cut-out device has been tripped. The additional light can warn the user that the fuse needs to be replaced, that the circuit breaker needs to be reset or that the apparatus should be allowed to stand unused for a short time to allow it to recover automatically.

During the incineration of a needle, the molten metal is prevented from adhering to the electrode 40 by the vibration of the latter caused by the crystal 42. Instead the debris falls off the electrode and collects in the debris compartment 50. The heat generated during the incineration will burn any liquid on the needle but the fumes and any aerosol will mostly be contained within the cartridge because the hole 32 will at this time be obstructed by the needle effectively sealing off the compartment 50. When the syringe is removed, the flaps of the membrane 29 return to their position shown in FIG. 1 to contain within the cartridge any fumes that may pass through the hole 32 when it ceases to be obstructed by the needle.

The incineration of the needle will blunt and sterilise the needle so that no injury can be caused to persons handling the waste hypodermic syringes. In most cases, the fusing of the needle material will also seal the hypodermic syringe.

When the compartment 50 is full, there will be an electrical path through the debris from the strip 44 at the top of the container to the similar strip in the base and this resistance is monitored in the main housing. When the debris fills the cartridge, the light 16 is switched on to warn the user that the cartridge should be replaced.

It should be emphasised that the above description is only given by way of example and that many modifications may be made to the apparatus without departing from the scope of the invention as set out in the appended claims.

For example, if a small cartridge is used, it is not necessary to provide a piezoelectric crystal to vibrate the stationary electrode. If a vibrator is provided, it is not necessary for it to be mounted in the cartridge and it can instead be mounted in the main housing In this case, the vibrations can be transmitted to the electrodes for example through a flexible membrane incorporated in the cartridge wall. Furthermore the cartridge may have a transparent region instead of the described electrical sensing of the level of the debris within the cartridge. It is not essential for one of the electrodes to be pivotable nor indeed movable as a short needle stub can be tolerated so long as it has been blunted and sterilised.

Various modifications may also be made in the construction of the cartridge and to the means for sealing it both while needle incineration is taking place and while the apparatus is standing idle. For example, a manually releasable cover may be provided for hermetically covering over the insertion aperture during periods when the apparatus is not in use.

What is claimed is:

1. A needle incineration apparatus for disposing of hypodermic needles comprising:
   a disposable cartridge having a wall formed with an insertion aperture through which a needle to be destroyed may be introduced into the apparatus, there being a sealed debris compartment within the cartridge,
   two spaced electrodes mounted in the cartridge within the sealed debris compartment and defining a gap between the electrodes, the gap being aligned with the insertion aperture,
   a main housing to which the disposable cartridge is separably attached, and
   a power supply disposed within the main housing and connected to the electrodes for applying a voltage across the electrodes to destroy needles introduced through the insertion aperture into the gap to contact the two electrodes.

2. An apparatus according to claim 1, comprising a bellows of elastomeric material fitted to the insertion aperture and a conical guide member mounted centrally to the bellows and having a central hole for passage of the needle into the debris compartment.

3. An apparatus according to claim 2, wherein the bellows has a mouth and the apparatus comprises a self-closing membrane across the mouth of the bellows.

4. An apparatus according to claim 3, wherein the self-closing membrane comprises a sheet of elastomeric material having one or more slits to define flaps that separate automatically during insertion of a syringe and return to a closed mating position when the syringe is withdrawn from the insertion aperture.

5. An apparatus according to claim 1, wherein one of the electrodes is mounted in such a manner as to be movable towards the other electrode to close the gap between the electrodes as the end of a needle is reached.

6. An apparatus according to claim 5, wherein the movable electrode is pivotably mounted within the cartridge.

7. An apparatus according to claim 1, wherein the cartridge has a transparent wall section to enable visual inspection of debris within the debris compartment.

8. An apparatus according to claim 1, comprising a means for sensing the level of debris within the debris compartment of the cartridge.

9. An apparatus according to claim 8, wherein the means for sensing the level of debris within the debris compartment comprises two additional spaced electrodes of which at least one is positioned in the cartridge near a maximum level of debris.

10. An apparatus according to claim 1, comprising interlocking formations formed on the cartridge and on the main housing.

11. A needle incineration apparatus for disposing of hypodermic needles comprising:
    a disposable cartridge having a wall formed with an insertion aperture through which a needle to be destroyed may be introduced into the apparatus, there being a permanently closed debris compartment within the cartridge,
    two spaced electrodes mounted in the cartridge within the permanently closed debris compartment and defining a gap between the electrodes, the gap being aligned with the insertion aperture,
    a main housing to which the disposable cartridge is separably attached,
    a power supply disposed within the main housing and connected to the electrodes for applying a voltage across the electrodes to destroy needles introduced through the insertion aperture into the gap to contact the two electrodes, and
    a vibrator means for vibrating at least one of the electrodes to inhibit build up of a deposit on the electrodes.

12. An apparatus according to claim 11, wherein the vibrator means is disposed within the cartridge.

13. An apparatus according to claim 12, wherein the vibrator means comprises a piezoelectric crystal adhered to said at least one electrode and a means disposed in the main housing for applying an excitation voltage to the piezoelectric crystal.

14. An apparatus according to claim 13, wherein the means for applying an excitation voltage to the piezoelectric crystal is operative to generate an alternating voltage having an ultrasonic frequency.

15. In or for use in a needle incineration apparatus having an electrical power supply disposed within a main housing, a cartridge releasably fitted to the main housing and comprising:

a container having an internal sealed debris compartment and a wall formed with an insertion aperture for enabling a needle to be inserted into the debris compartment, a bellows of elastomeric material fitted to the insertion aperture, a conical guide member mounted centrally to the bellows and having a central hole for passage of the needle into the debris compartment, two electrodes disposed within the debris compartment to be contacted by the needle when it is inserted into the debris compartment through the insertion aperture, and at least one electrical connector on the exterior of the container for connecting the electrodes in the debris compartment to the electrical power supply in the main housing when the cartridge is fitted to the housing.

16. A cartridge according to claim 15, wherein the bellows has a mouth and the apparatus comprises a self-closing membrane across the mouth of the bellows.

17. A cartridge according to claim 16, wherein the self-closing membrane comprises a sheet of elastomeric material having one or more slits to define flaps that separate automatically during insertion of a syringe and return to a closed mating position when the syringe is withdrawn from the insertion aperture.

18. In or for use in a needle incineration apparatus having an electrical power supply disposed within a main housing, a cartridge releasably fitted to the main housing and comprising:

a container having an internal sealed debris compartment and a wall formed with an insertion aperture for enabling a needle to be inserted into the debris compartment, two electrodes disposed within the debris compartment to be contacted by the needle when it is inserted into the debris compartment through the insertion aperture, and at least one electrical connector on the exterior of the container for connecting the electrodes in the debris compartment to the electrical power supply in the main housing when the cartridge is fitted to the housing, wherein one of the electrodes is mounted in such a manner as to be movable towards the other electrode to close the gap between the electrodes as the end of a needle is reached, the movable electrode being pivotably mounted within the cartridge.

19. A cartridge according to claim 15, having a formation for interlocking engagement with a complementary formation of the main housing to provide a firm mechanical connection of the cartridge to the main housing.

20. In or for use in a needle incineration apparatus having an electrical power supply disposed within a main housing, a cartridge releasably fitted to the main housing and comprising:

a container having an internal sealed debris compartment and a wall formed with an insertion aperture for enabling a needle to be inserted into the debris compartment, two electrodes disposed within the debris compartment to be contacted by the needle when it is inserted into the debris compartment through the insertion aperture, and at least one electrical connector on the exterior of the container for connecting the electrodes in the debris compartment to the electrical power supply in the main housing when the cartridge is fitted to the housing, and wherein the cartridge has a transparent wall section to enable visual inspection of debris within the debris compartment.

21. In or for use in a needle incineration apparatus having an electrical power supply disposed within a main housing, a cartridge releasably fitted to the main housing and comprising;

a container having an internal sealed debris compartment and a wall formed with an insertion aperture for enabling a needle to be inserted into the debris compartment, two electrodes disposed within the debris compartment to be contacted by the needle when it is inserted into the debris compartment through the insertion aperture, and at least one electrical connector on the exterior of the container for connecting the electrodes in the debris compartment to the electrical power supply in the main housing when the cartridge is fitted to the housing, and a sensing means for sensing level of debris within the debris compartment, the sensing means comprising two additional spaced electrodes of which at least one is positioned in the cartridge near a maximum level of debris, the connector on the exterior of the cartridge serving to connect the sensing means to a circuit within the main housing of the needle incineration apparatus for measuring electrical resistance between the sensor electrodes.

22. In or for use in a needle incineration apparatus having an electrical power supply disposed within a main housing, a cartridge releasably fitted to the main housing and comprising:

a container having an internal permanently closed debris compartment and a wall formed with an insertion aperture for enabling a needle to be inserted into the debris compartment, two electrodes disposed within the debris compartment to be contacted by the needle when it is inserted into the debris compartment through the insertion aperture, at least one electrical connector on the exterior of the container for connecting the electrodes in the debris compartment to the electrical power supply in the main housing when the cartridge is fitted to the housing, and a vibrator means within the container for vibrating at least one of the electrodes to inhibit build up of a deposit on the electrodes, and wherein the connector on the exterior of the container serves further to connect the vibrator means to receive an excitation voltage.

23. A cartridge according to claim 22, wherein the vibrator means comprises a piezoelectric crystal adhered to said at least one electrode.

* * * * *